United States Patent [19]

Wood et al.

[11] Patent Number: 4,609,679

[45] Date of Patent: Sep. 2, 1986

[54] PROCESS FOR PRODUCING METHANE FROM HYDROGEN AND CARBON MONOXIDE

[75] Inventors: Clayton D. Wood, Framingham, Mass.; Edward F. Gleason, Berkeley, Calif.

[73] Assignee: The Dow Chemical Company, Midland, Mich.

[21] Appl. No.: 739,944

[22] Filed: May 31, 1985

[51] Int. Cl.$^4$ ................................................ C07C 1/04
[52] U.S. Cl. .................................... 518/715; 502/326
[58] Field of Search ........................................ 518/715

[56] References Cited

U.S. PATENT DOCUMENTS

| | | |
|---|---|---|
| 2,553,398 | 5/1951 | Atwell . |
| 2,583,611 | 1/1952 | Sullivan . |
| 2,616,914 | 11/1952 | Riblett . |
| 3,988,334 | 10/1976 | Finch et al. . |
| 4,042,614 | 8/1977 | Vannice et al. . |
| 4,149,998 | 4/1979 | Tauster et al. . |
| 4,171,320 | 10/1979 | Vannice et al. . |
| 4,206,135 | 6/1980 | Kugler et al. . |
| 4,269,737 | 5/1981 | Grenoble et al. . |
| 4,477,595 | 10/1984 | Madon ................................ 518/715 |

OTHER PUBLICATIONS

Bull. Chem. Soc. Japan, vol. 55, 2653–2654 (1982).
Mills & Steffgen, Catalysis Reviews, vol. 8, No. 2, (1973), pp. 159–210.
Journal of Catalysis, vol. 63, pp. 255–260, (1980).
Hydrocarbon Processing, pp. 107–112, Apr., 1980.
Chemical & Engineering News, p. 30, Apr. 5, 1982.
*Journal of Catalysis*, vol. 40, pp. 173–183 (1975).
*Stud. Surf. Sci. Catal.*, Trimm & Karal, pp. 517–528 (1981).
*I&EC Product Res. & Development*, vol. 4, pp. 265–269 (1965).
*Platinum Metals Review*, vol. 25, No. 2, pp. 50–56 (1981).
*Surface Technology*, vol. 14, pp. 65–72 (1981).
*Journal of Catalysis*, vol. 53, pp. 186–197 (1978).
*Journal of Catalysis*, vol. 37, pp. 449–461, 462–473 (1975).
*Journal of Catalysis*, vol. 55, pp. 29–35 (1978).
*Journal of the Chem. Soc.*, "Chem. Commun.", pp. 955–956 (1982).
Chemical Abstract 53:12610e.
Chemical Abstract 53:22613h.
Chemical Abstract 55:9802e.
Chemical Abstracts 77:130104n.
Chemical Abstracts 79:116805b.
Chemical Abstracts 80:82039h.
Chemical Abstracts 82:88179s.
Chemical Abstracts 82:142195j.
Chemical Abstracts 83:62776e.
Chemical Abstracts 85:38803g.
Chemical Abstracts 86:57918k.
Chemical Abstracts 86:149320n.
Chemical Abstracts 87:143303h.
Chemical Abstracts 87:207266h.
Chemical Abstracts 89:69893y.
Chemical Abstracts 89:224639r.
Chemical Abstracts 90:12837z.
Chemical Abstracts 90:108451v.
Chemical Abstracts 91:41793h.
Chemical Abstracts 91:195752f.
Chemical Abstracts 92:8790c.
Chemical Abstracts 92:44581u.
Chemical Abstracts 93:81307a.
Chemical Abstracts 93:81308b.
Chemical Abstracts 93:134809z.
Chemical Abstracts 93:167287f.
Chemical Abstracts 94:124224m.
Chemical Abstracts 95:172346v.
Chemical Abstracts 95:192809b.
Chemical Abstracts 87:207272g.

*Primary Examiner*—Howard T. Mars
*Attorney, Agent, or Firm*—Paul D. Hayhurst; Paul M. Bork

[57] ABSTRACT

Selectively produce methane under Fischer-Tropsch conditions using a catalyst consisting essentially of ruthenium supported on an oxide of tantalum, niobium, vanadium or mixtures thereof, the support preparation including calcination at a temperature such that essentially no crystalline metal oxide is detectable by X-ray diffraction prior to deposition of the catalytic metal.

12 Claims, No Drawings

PROCESS FOR PRODUCING METHANE FROM HYDROGEN AND CARBON MONOXIDE

BACKGROUND OF THE INVENTION

This invention relates to an improved Fischer-Tropsch process for the production of methane. More specifically, it relates to such a process which employs a supported ruthenium catalyst.

The art contains many examples of metals known to be useful in reacting carbon monoxide with hydrogen to produce a variety of compounds, including hydrocarbons and oxygenated compounds. These metals include, among others, Mo, W, Rh, Ru, Re, Pd, Ni, Co and Fe. In what has come to be called the Fischer-Tropsch Synthesis, carbon monoxide and hydrogen are reacted over a metal catalyst to produce saturated and unsaturated hydrocarbons and oxygenated compounds containing from 1 to as many as 1000 carbon atoms. The hydrocarbons can be aliphatic, alicyclic or aromatic. Commercial utilization of this synthesis prior to 1950 was accomplished largely in Germany and is summarized in Storch, Columbic and Anderson: *The Fischer-Tropsch and Related Synthesis*, John Wiley and Sons, New York 1951.

Ruthenium has been acknowledged to be the most active catalytic metal for the production of methane from $H_2$ and CO. *Catalysis Reviews*, V.8, No.2, 159–210, at 181 (1973). Ruthenium catalysts having Group VB oxide supports are generally known. For example, U.S. Pat. No. 4,149,998 discloses a catalyst composition consisting of selected Group VIII metals supported on oxides of Group IVB or VB. Yet the majority of prior art Fischer-Tropsch processes and catalysts are not capable of selectively producing methane.

U.S. Pat. No. 4,171,320 discloses a catalyst comprising ruthenium on a crystalline support. The support is required to contain an oxide of a Group VB metal, e.g., tantalum. The catalysts are taught to be useful for the selective conversion of $H_2$ and CO into olefins of from 2 to 5 carbon atoms.

Heretofore, a method for the high yield production of methane from $H_2$ and CO using ruthenium supported on an oxide of a Group VB metal has not been disclosed.

SUMMARY OF THE INVENTION

The present invention is a process for producing hydrocarbons by contacting carbon monoxide and hydrogen at reactive conditions, the improvement comprising increasing the yield of methane by contacting the carbon monoxide and hydrogen with a catalyst consisting essentially of:

(a) a catalytic metal component which is from about 0.1 to about 10 percent by weight, based on the weight of the catalyst, of ruthenium; and the balance being (b) a support component which is at least one oxide of tantalum, niobium, vanadium or mixtures thereof, the support preparation including calcination at a temperature such that essentially no crystalline metal oxide is detectable by X-ray diffraction prior to deposition of the catalytic metal thereon.

Surprisingly, the process of the present invention selectively produces methane in high yields from $H_2$ and CO, does not require high pressures, and can operate at relatively low ratios of $H_2$ to CO.

DETAILED DESCRIPTION OF THE INVENTION

The process of the present invention can produce methane in high yields from $H_2$ and CO using a ruthenium catalyst having a support prepared as described hereinbelow.

The carbon monoxide required for the process can be obtained from any carbon source, such as from the degradation of coal. The molar ratio of hydrogen to carbon monoxide ranges generally from at least about 0.5 to about 10, and preferably is from about 1 to about 3. The hydrogen can be produced from the gasification of coal, commercially pure hydrogen or hydrogen from any other commercially acceptable source, e.g., that produced in the dehydrogenation of alkanes. Diluent gases, such as nitrogen, can be included if desired. Conveniently, as is known in the art, synthesis gas can be employed as the source of both the carbon monoxide and hydrogen feed materials.

The catalyst of the present invention includes a catalytic amount of ruthenium, supported on at least one oxide of tantalum, niobium, vanadium or mixtures of these oxides. Typically, the active catalyst will contain from about 0.1 to about 10 weight percent ruthenium, based on the total weight of the catalyst. Preferably, the active catalyst will contain from about 0.5 to about 5 weight percent ruthenium. The remainder of the catalyst is a support component which is an oxide of tantalum, niobium or vanadium. Mixtures of these oxides can be employed as the support component.

The support component can be prepared using techniques well-known in the art except that it must be calcined, at a temperature such that essentially no crystalline metal oxide phase is present as determined by X-ray diffraction techniques, prior to depositing the catalytic ruthenium component thereon. Recall that the examples of U.S. Pat. No. 4,171,320 disclose crystalline metal oxide in the support. The catalytic support component advantageously is an oxide of a metal of Group VB, i.e., vanadium, niobium (also called columbium) and tantalum. Oxides of tantalum are preferred. Tantala (tantalum oxide) supports of the present invention are typically calcined at from about 100° C. to about 550° C. Preferably, tantala supports are calcined at from about 400° C. to about 500° C. The calcined support typically has a surface area greater than about 10 m²/g, preferably 20 to 200 m²/g, and most preferably from about 30 to 120 m²/g prior to the deposition of the ruthenium precursor. These surface areas are as measured by the Brunauer-Emmett-Teller (BET) method. The BET method is described by R. B. Anderson in *Experimental Methods in Catalytic Research*, pp. 48–66, Academic Press, 1968.

The catalytic ruthenium is deposited on the support component via methods known in the art such as, for example, impregnation of the support with a salt of the catalytic metal. A ruthenium precursor, i.e., a compound which can be reduced to ruthenium metal, is converted to ruthenium metal by exposing the precursor to a reducing atmosphere via methods known in the art. It is preferred to reduce the ruthenium precursor in situ, i.e., while the precursor is in the reaction vessel. Typically, the precursor is an organic or inorganic salt of ruthenium. Examples of precursors include $RuCl_3 \cdot 3H_2O$, and other halides of ruthenium.

The process conditions of the process of the present invention are typical for Fischer-Tropsch synthesis.

Process reaction conditions can vary over a rather wide range. The pressure can vary from at least about 1 (0.1 MPa) up to about 100 (10 MPa) atmospheres. Preferably, a pressure of from about 1 (0.1 MPa) to about 5 (0.5 MPa) atmospheres is employed. Atmospheric ambient pressure is most preferred. The reaction temperature typically ranges from about 200° C. to about 400° C. and preferably is from about 250° C. to about 350° C.

When CO and $H_2$ are contacted in the presence of a catalyst as described hereinabove, methane surprisingly is produced with simultaneous high selectivity and conversion, i.e., in high yield, versus the low yield of methane taught in U.S. Pat. No. 4,171,320 using a similar catalyst. For the purposes of the present invention, the term "yield" means the numerical product of conversion of carbon monoxide and selectivity to methane based on the total of carbon compounds in the reactor effluent. Desirably, the yield of methane from the product of the present invention is at least about 25 percent; preferably, the yield is at least about 55 percent; most preferably, the yield is at least about 85 percent.

SPECIFIC EMBODIMENTS

The following examples and comparative experiments are given to illustrate the invention and should not be construed as limiting its scope. All parts and percentages are by weight unless otherwise indicated.

Preparation 1

A solution is prepared by dissolving 20 g of tantanum pentaisopropoxide in 200 ml of isopropanol. A second solution is prepared by adding 50 ml of isopropanol to 50 ml of 6 molar aqueous ammonium hydroxide. The second solution is slowly added to the first solution at 0° C. The hydrolyzed material precipitates and is isolated by filtration, is washed with several 100-ml portions of water, and is dried overnight in air at 110° C. The dried tantala is then calcined at 450° C. for 15 hours to give a material with a BET surface area of approximately 120 $m^2/g$.

Preparation 2

The alumina employed is gamma-alumina, and is obtained from Strem Chemicals and is calcined at 450° C. for about 5 hours. The surface area is 93 $m^2/g$ and the X-ray diffraction pattern is characteristic of gamma-alumina.

Preparation 3

A solution of 100 g of titanium tetraisopropoxide in 500 ml of isopropanol is prepared. A second solution of equivoluminar portions of isopropanol and water having a total volume of 300 ml is slowly added to the first solution at 0° C. A precipitate forms. The precipitate is isolated by filtration, is washed with several 500-ml portions of water, and is dried overnight in air at 110° C. The $TiO_2$ is calcined at 400° C. for 5 hours and the X-ray diffraction analysis of the solid shows a pure anatase phase.

Preparation 4

Five grams of the tantala prepared as described in Preparation 1 is added to 100 ml of an aqueous solution containing 0.64 g of $RuCl_3.1-3H_2O$. The resulting mixture is stirred for 1 hour and the water is removed in vacuo. The resulting catalyst is dried overnight in air at 110° C., and is determined to contain approximately 5 weight percent ruthenium. No crystalline tantalum oxide is observed in the catalyst using X-ray diffraction techniques.

Preparation 5

A $Ru/Al_2O_3$ catalyst is prepared using the procedure of Preparation 4 except that the alumina of Preparation 2 is substituted for tantala.

Preparation 6

A $Ru/TiO_2$ catalyst is prepared using the procedure of Preparation 4 except that the titania of Preparation 3 is substituted for alumina.

General Reaction Procedure

A 16-inch long piece of 9/16 inch tubing of type 316 stainless steel is employed vertically as a reactor. The reactor is equipped with a means for temperature control, and has 1 g of catalyst held in place by quartz wool in the center of the reactor. The catalyst is reduced in situ at 400° C. for 15 hours with hydrogen at 50 cc/min. Then the reactor is cooled to 300° C. in flowing hydrogen gas. Then a feed stream of 50 cc/min $H_2$ and 50 cc/min CO is fed to the reactor under a pressure of approximately 1 atmosphere (100 kPa) (gas hourly space velocity=6000/hr). The product stream is analyzed using gas chromatographic methods capable of detecting $C_{1-5}$ hydrocarbons, $C_{1-5}$ alcohols, $H_2$, CO and $CO_2$.

EXAMPLES 1-6

The General Reaction Procedure is employed using the Ru/tantala catalyst of Preparation 4. The results are summarized in Tables I and II.

COMPARATIVE EXPERIMENTS 1-3

The General Reaction Procedure is repeated using comparative catalysts prepared according to the methods of Preparations 5 and 6. The results are summarized in Table I.

TABLE I

| Run | Catalyst | Temp. (°C.) | Pres (psig) | Molar $H_2$/CO Ratio | % CO Conv | Mole % $CH_4$ Effluent | $CH_4$ % Yield | Mole % $CO_2$ Effluent |
|---|---|---|---|---|---|---|---|---|
| C. E. 1a | $Ru/Al_2O_3$ | 300 | 14.7 | 1 | 45 | 60 | 27 | 40 |
| C. E. 1b | $Ru/TiO_2$ | 300 | 14.7 | 1 | 40 | 60 | 24 | 40 |
| Ex. 1 | Ru/Tantala | 300 | 14.7 | 1 | 73 | 50 | 36.5 | 50 |
| C. E. 2 | $Ru/Al_2O_3$ | 300 | 14.7 | 2 | 55 | 76 | 41.8 | 23 |
| Ex. 2 | Ru/Tantala | 300 | 14.7 | 2 | 99 | 67 | 66.3 | 32 |
| C. E. 3 | $Ru/Al_2O_3$ | 250 | 300 | 2 | 58 | 82 | 47.6 | 16 |
| Ex. 3 | Ru/Tantala | 250 | 300 | 2 | 98 | 67 | 65.7 | 33 |

The results summarized in Table I indicate the unexpected superiority of noncrystalline tantala as a catalytic support in the selective production of methane from $H_2$ and CO.

TABLE II

| Run | Temp (°C.) | Pres (psig) | Molar H$_2$/CO Ratio | % CO Conv | Mole % CH$_4$ Effluent | CH$_4$ % Yield | Mole % CO$_2$ Effluent |
| --- | --- | --- | --- | --- | --- | --- | --- |
| Ex. 1 | 300 | 14.7 | 1 | 73 | 50 | 36.5 | 50 |
| Ex. 2 | 300 | 14.7 | 2 | 99 | 67 | 66.3 | 32 |
| Ex. 3 | 250 | 300 | 2 | 98 | 67 | 65.7 | 33 |
| Ex. 4 | 250 | 14.7 | 2 | 98 | 67 | 65.7 | 33 |
| Ex. 5 | 200 | 14.7 | 1 | 52 | 50 | 26.0 | 50 |
| Ex. 6 | 200 | 530 | 2 | 70 | 82 | 57.4 | 10 |
| Ex. 7 | 200 | 530 | 3 | 93 | 93 | 86.5 | 7 |

Table II exemplifies the process of the present invention at varying reaction conditions.

What is claimed is:

1. In a process for producing hydrocarbons by contacting carbon monoxide and hydrogen at reactive conditions, the improvement comprising increasing the yield of methane by contacting the carbon monoxide and hydrogen with a catalyst consisting essentially of:
   (a) a catalytic metal component which is from about 0.1 to about 10 percent by weight, based on the weight of the catalyst, of ruthenium; and the balance being
   (b) a support component which is at least one oxide of tantalum, niobium, vanadium or mixtures thereof, the support preparation including calcination at a temperature such that essentially no crystalline metal oxide is detectable by X-ray diffraction prior to deposition of the catalytic metal thereon.

2. The process of claim 1 wherein the support component is an oxide of tantalum.

3. The process of claim 2 wherein the ratio of hydrogen to carbon monoxide ranges from about 1 to about 3.

4. The process of claim 2 wherein the support component has a surface area greater than about 10 m$^2$/g.

5. The process of claim 1 wherein the yield is at least 25 percent.

6. The process of claim 4 wherein the catalytic metal component is from about 0.5 to about 5 percent by weight.

7. The process of claim 1 wherein the contacting is at a temperature of from about 200° C. to about 400° C.

8. The process of claim 3 wherein the hydrogen to carbon monoxide ratio is 2 and the pressure is ambient.

9. The process of claim 1 wherein the yield is at least 55 percent.

10. The process of claim 2 wherein the yield is at least about 85 percent.

11. The process of claim 1 wherein the support is calcined at from about 100° C. to about 550° C.

12. In a process for producing methane by contacting carbon monoxide and hydrogen at reactive conditions, the improvement comprising contacting the carbon monoxide and hydrogen with a catalyst composition consisting essentially of:
   (a) from about 0.1 to about 10 percent by weight, based on the weight of the composition, ruthenium; and
   (b) a support component which is at least one non-crystalline oxide of tantalum, niobium, vanadium or mixtures thereof,
the support preparation including calcination at a temperature such that essentially no crystalline metal oxide is detectable by X-ray diffraction prior to deposition of the catalytic metal thereon under conditions sufficient to produce a yield of at least about 25 percent.

* * * * *